(12) United States Patent
Meier et al.

(10) Patent No.: US 9,626,719 B2
(45) Date of Patent: Apr. 18, 2017

(54) DISPLAYING A SERIES OF REPORTS WITHIN A SINGLE USER INTERFACE

(75) Inventors: Brian A. Meier, Fargo, ND (US); Robert J. Wagner, Fargo, ND (US); Nicholas A. Bigelow, Lincoln, NE (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 191 days.

(21) Appl. No.: 12/985,162

(22) Filed: Jan. 5, 2011

(65) Prior Publication Data

US 2012/0174027 A1 Jul. 5, 2012

(51) Int. Cl.
*G06Q 40/00* (2012.01)
*G06F 19/00* (2011.01)
*G06F 3/0485* (2013.01)

(52) U.S. Cl.
CPC ......... *G06Q 40/00* (2013.01); *G06F 3/04855* (2013.01); *G06F 19/321* (2013.01)

(58) Field of Classification Search
CPC .... G06F 19/321; G06F 3/04855; G06Q 40/00
USPC .......................................................... 715/786
See application file for complete search history.

(56) References Cited

U.S. PATENT DOCUMENTS

| | | | |
|---|---|---|---|
| 6,877,135 B1 * | 4/2005 | Kamiwada | G06F 3/0482 707/999.003 |
| 7,283,909 B1 * | 10/2007 | Olsen | G09B 29/007 702/2 |
| 7,634,724 B2 | 12/2009 | Welcker et al. | 715/243 |
| 2002/0188486 A1 | 12/2002 | Gil et al. | |
| 2002/0198781 A1 | 12/2002 | Cobley | |
| 2005/0185607 A1 | 8/2005 | Svensson et al. | |
| 2005/0216421 A1 | 9/2005 | Barry et al. | |
| 2005/0253874 A1 | 11/2005 | Lal et al. | 345/661 |
| 2005/0267868 A1 | 12/2005 | Liebl et al. | 707/2 |
| 2006/0015416 A1 | 1/2006 | Hoffman et al. | |
| 2006/0048048 A1 | 3/2006 | Welcker et al. | |
| 2006/0141430 A1 * | 6/2006 | Hutchinson et al. | 434/236 |
| 2006/0241962 A1 | 10/2006 | Flora et al. | 705/1 |
| 2007/0256028 A1 | 11/2007 | Hays et al. | 715/825 |
| 2008/0027878 A1 | 1/2008 | Street et al. | |
| 2008/0046805 A1 | 2/2008 | Shewchenko et al. | 715/215 |
| 2008/0114847 A1 | 5/2008 | Ma et al. | |

(Continued)

OTHER PUBLICATIONS

Google Picasa 3: The Basics; 2009; Indiana Univeristy, University Information Technology Services; v1.0.0, pp. 12, 19 and 26.*

(Continued)

*Primary Examiner* — Jennifer To
*Assistant Examiner* — Ashley Fortino

(57) ABSTRACT

A user interface may be provided for displaying a series of reports. The user interface may include a primary report area, a secondary report area and a navigation slider. The primary report area may be utilized to display a selected report image associated with a report in a report series. The secondary report area may be utilized to display one or more additional report images associated with other reports in the report series. The navigation slider may be utilized to navigate among the report images displayed in the secondary report area. The report images displayed in the primary and secondary report areas may be manipulated by one or more user commands received in the user interface.

20 Claims, 6 Drawing Sheets

(56) References Cited

U.S. PATENT DOCUMENTS

| | | | |
|---|---|---|---|
| 2009/0100321 A1* | 4/2009 | Singh | G06F 3/0482 715/205 |
| 2009/0138316 A1 | 5/2009 | Weller et al. | |
| 2009/0172543 A1* | 7/2009 | Cronin et al. | 715/721 |
| 2009/0228485 A1 | 9/2009 | Handy et al. | 707/7 |
| 2010/0030075 A1* | 2/2010 | Lee | 600/437 |
| 2010/0198649 A1 | 8/2010 | Appleyard et al. | 705/9 |
| 2012/0173294 A1 | 7/2012 | Olson et al. | |

OTHER PUBLICATIONS

U.S. Office Action mailed Dec. 8, 2011 in U.S. Appl. No. 12/985,208, 14 pages.

U.S. Office Action mailed Mar. 14, 2012 in U.S. Appl. No. 12/985,208, 15 pages.

U.S. Appl. No. 12/985,208, filed Jan. 5, 2011, entitled "Integrating Report Actions for a Series of Reports within a Single User Interface," Inventors: Jennifer F. Olson, Brian A. Meier, Jay F. Winkis, Robert J. Wagner.

Hernandez, "Data Visualization and BI Dashboards—Actionable Dashboards"—Published Date: Jul. 22, 2009, 4 pp. http://www.akgroup.com/Blogs/Lists/Posts/ViewPost.aspx?ID=73.

Report Viewer Limited, "The report viewer 4.0.5," Published Apr. 24, 2010, 2 pp., http://www.dodownload.com/business+manage/other+business/report+viewer+for+crystal+reports.html.

Hari Sharma, "Types of SSRS reports," Published Jul. 2, 2010, 4 pp., http://sql-bi-dev.blogspot.com/2010/07/types-of-ssrs-reports.html.

Information Builders, "Webfocus business intelligence dashboard," Published Dec. 3, 2005, 2 pp., http://www.informationbuilders.com/products/webfocus/analytic_dashboard.html.

SAP Business One, "Integrating crystal reports with sap business one," Published 2009, 4 pp., http://download.sap.com/download.epd?context=1ABE54831297AE176E19C3A40E0AE102A3854B6CC746F73AED5C938B9E52A8BF085C4C3DEA3ED7A580390E55E252F6997670D772882B5ED6.

Dimensional Insight, "Empowering a sales organization with role-based dashboards and self-service reporting," Published 2009, 2 pp., http://www.dimins.com/62_launch/pdfs/lipman.pdf.

Microsoft Dynamics, "Deploy a complete point of sale solution with Microsoft Dynamics Retail Management System (RMS)," Published 2010, 4 pp., http://www.microsoft.com/dynamics/en/us/products/rms-overview.aspx.

Oracle Fusion Middleware, "Introduction to the action form view," Published May 2009, 32 pp., http://download.oracle.com/docs/cd/E12839_01/integration.1111/e10230/view_ref.htm#CACCDFFA.

Emptoris, "Actionable visibility: anyone, anytime, anywhere," Published 2010, 3 pp., http://www.emptoris.com/solutions/actionable_visibility.asp.

Prevolac, "Modifying the system using Microsoft Dynamics NAV 2009: Part 2," Published Aug. 2009, 13 pp., http://www.packtpub.com/article/modifying-system-microsoft-dynamics-nav-2009-part-2.

Business Objects, "Crystal Reports 2008 what's new," Published 2008, 4 pp., http://87.229.26.143/download/crystal/doc/cr_2008_whats_new.pdf.

U.S. Appl. No. 12/985,208, Office Action mailed Mar. 6, 2015, 28 pgs.

* cited by examiner

DISPLAYING A SERIES OF REPORTS WITHIN A SINGLE USER INTERFACE

CROSS-REFERENCE TO RELATED APPLICATIONS

This application is related to U.S. utility patent application entitled "Integrating Report Actions for a Series of Reports within a Single User Interface" having Ser. No. 12/985,208, which was filed on Jan. 5, 2011. The aforementioned application is entirely incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Business enterprises may utilize enterprise resource planning ("ERP") and customer relationship management ("CRM") software applications to organize, automate, and synchronize business processes, including data related to sales activities, marketing, human resources, customer service and technical support. The aforementioned business processes often result in the generation of various reports which may be utilized by administrators or other business personnel to facilitate the management of business data. For example, various reports may be generated to show historical changes in a particular business metric (such as sales data) over a user-specified time period. Data from these reports may then be visually presented to a user as a snapshot (e.g., a graph). However, current applications are unable to provide multiple snapshots of report data in a single view. Furthermore, users must navigate away from an application displaying a snapshot in order to access one or more different applications to initiate actions which are relevant to the report data upon which the snapshot is based. It is with respect to these considerations and others that the various embodiments of the present invention have been made.

SUMMARY

This summary is provided to introduce a selection of concepts in a simplified form that are further described below in the Detailed Description. This summary is not intended to identify key features or essential features of the claimed subject matter, nor is it intended as an aid in determining the scope of the claimed subject matter.

Embodiments are provided for displaying a series of reports in a single user interface. The user interface may include a primary report area, a secondary report area and a navigation slider. The primary report area may be utilized to display a selected report image associated with a report in a report series. The secondary report area may be utilized to display one or more additional report images associated with other reports in the report series. The navigation slider may be utilized to navigate among the report images displayed in the secondary report area. The report images displayed in the primary and secondary report areas may be manipulated by one or more user commands received in the user interface.

These and other features and advantages will be apparent from a reading of the following detailed description and a review of the associated drawings. It is to be understood that both the foregoing general description and the following detailed description are illustrative only and are not restrictive of the invention as claimed.

DETAILED DESCRIPTION

Embodiments are provided for displaying a series of reports in a single user interface. The user interface may include a primary report area, a secondary report area and a navigation slider. The primary report area may be utilized to display a selected report image associated with a report in a report series. The secondary report area may be utilized to display one or more additional report images associated with other reports in the report series. The navigation slider may be utilized to navigate among the report images displayed in the secondary report area. The report images displayed in the primary and secondary report areas may be manipulated by one or more user commands received in the user interface.

Figure 1:
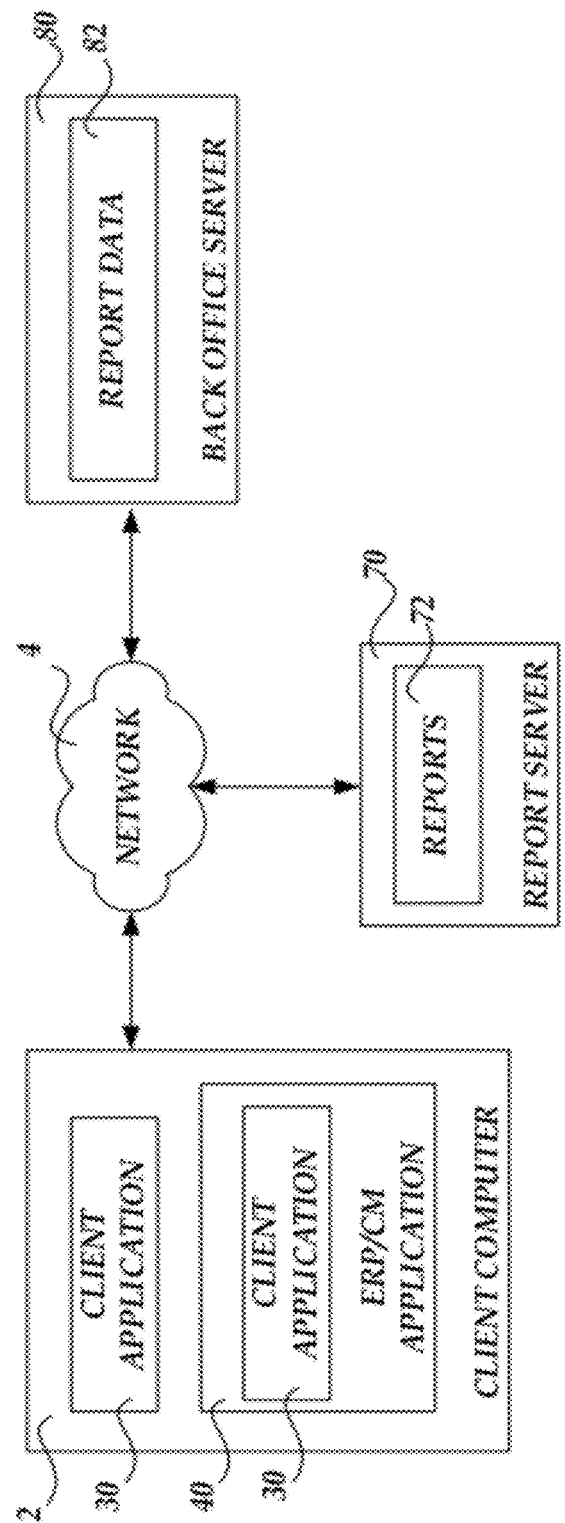
FIG. 1 is a block diagram illustrating a network architecture for displaying a series of reports within a single user interface, in accordance with various embodiments.

FIG. 1 is a block diagram illustrating a network architecture for displaying a series of reports within a single user interface, in accordance with various embodiments. The network architecture includes a client computer 2 in communication with a report server 70 which is in communication with a back office server 80 over a network 4. The network 4 may include a local network or a wide area network (e.g., the Internet). The client computer 2 may include a client application 30 or alternatively, an ERP/CM application 40 which includes the client application 30.

As will be described in greater detail with below respect to FIGS. 3-6, the client application 30 may comprise a software application operative to generate a user interface for displaying one or more reports as report images. The user interface may also include a secondary report area for displaying images of other reports which may be related to a primary report displayed in a primary report area and a slider control for navigating among the report images in the secondary report area.

In accordance with an embodiment, the ERP/CM application 40 may comprise an enterprise resource planning ("ERP") and customer relationship management ("CRM")

software application which may be utilized to organize, automate, and synchronize business processes, including, but not limited to, data related to sales activities, marketing, human resources, customer service and technical support. The ERP/CM application 40 may optionally include the client application 30, discussed above. It should be understood, that in accordance with various embodiments, the client application 30 may act as a stand-alone application or may be utilized with the ERP/CM application 40. In accordance with an embodiment, the client application 30 and the ERP/CM application 40 may comprise the DYNAMICS line of ERP and CM software applications developed by MICROSOFT CORPORATION of Redmond, Wash. It should be appreciated, however, that ERP and/or CRM applications from other manufacturers may also be utilized in accordance with the various embodiments described herein.

The report server 70 may be utilized to store reports 72 which are generated from report data. The reports 72 may comprise various reports related to business processes such as sales reports, marketing reports, human resources reports, customer service reports and technical support reports. The reports 72 may also include other reports not enumerated in the aforementioned list which are related to enterprise resource planning and customer relationship management in an organization. In accordance with an embodiment, the report server 70 may comprise a database server such as the SQL SERVER relational model database server marketed by MICROSOFT CORPORATION of Redmond, Wash. It should be appreciated, however, that database servers from other manufacturers may also be utilized in accordance with the various embodiments described herein.

The back office server 82 may be utilized to store report data 82. The report data 82 may be utilized by the client application 30 and the ERP/CM application 40 to generate the reports 72 which are stored on the report server 70. As should be understood by those skilled in the art, a "back office" may include a part of a corporation or other business enterprise where tasks dedicated to running the company itself take place.

Exemplary Operating Environment

Figure 2:
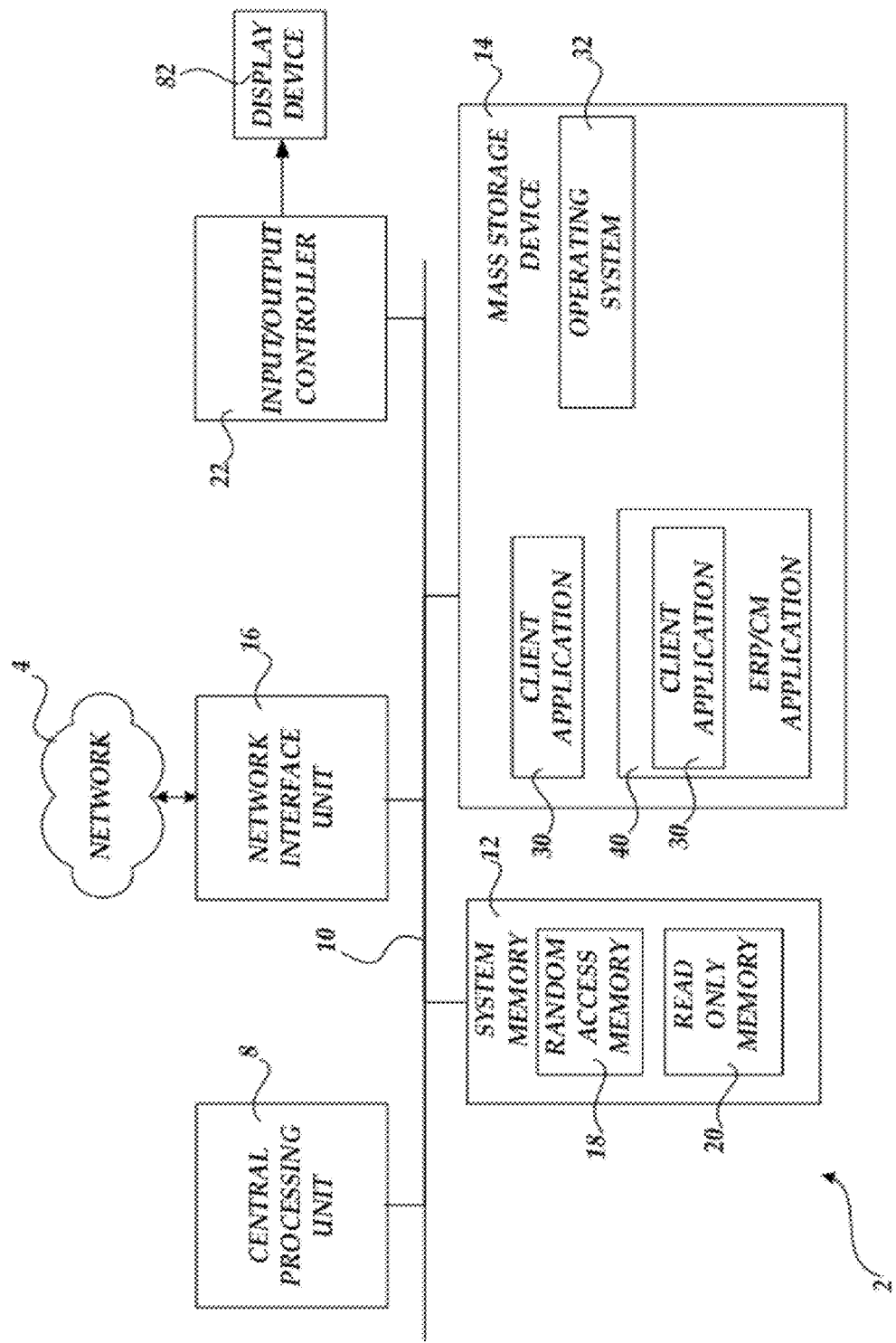
FIG. 2 is a block diagram illustrating a computing environment which may be utilized for displaying a series of reports within a single user interface, in accordance with an embodiment.

Referring now to FIG. 2, the following discussion is intended to provide a brief, general description of a suitable computing environment in which various illustrative embodiments may be implemented. While various embodiments will be described in the general context of program modules that execute in conjunction with program modules that run on an operating system on a computer, those skilled in the art will recognize that the various embodiments may also be implemented in combination with other types of computer systems and program modules.

Generally, program modules include routines, programs, components, data structures, and other types of structures that perform particular tasks or implement particular abstract data types. Moreover, those skilled in the art will appreciate that the various embodiments may be practiced with a number of computer system configurations, including handheld devices, multiprocessor systems, microprocessor-based or programmable consumer electronics, minicomputers, mainframe computers, and the like. The various embodiments may also be practiced in distributed computing environments where tasks are performed by remote processing devices that are linked through a communications network. In a distributed computing environment, program modules may be located in both local and remote memory storage devices.

FIG. 2 shows the client computer 2 which may include a general purpose desktop, laptop, tablet, or other type of computer capable of executing one or more application programs. The client computer 2 includes at least one central processing unit 8 ("CPU"), a system memory 12, including a random access memory 18 ("RAM") and a read-only memory ("ROM") 20, and a system bus 10 that couples the memory to the CPU 8. A basic input/output system containing the basic routines that help to transfer information between elements within the computer, such as during startup, is stored in the ROM 20.

The client computer 2 further includes a mass storage device 14 for storing an operating system 32 and the client application 30 (or optionally, the ERP/CM application 40 which incorporates the client application 30). In accordance with various embodiments, the operating system 32 may be suitable for controlling the operation of a networked computer, such as the WINDOWS operating systems from MICROSOFT CORPORATION of Redmond, Wash. The mass storage device 14 is connected to the CPU 8 through a mass storage controller (not shown) connected to the bus 10. The mass storage device 14 and its associated computer-readable media provide non-volatile storage for the client computer 2. The term computer-readable media as used herein may include computer storage media. Computer storage media may include volatile and nonvolatile, removable and non-removable media implemented in any method or technology for storage of information, such as computer readable instructions, data structures, program modules, or other data. Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by the client computer 2. Any such computer storage media may be part of the client computer 2.

The term computer-readable media as used herein may also include communication media. Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

According to various embodiments, the client computer 2 may operate in a networked environment using logical connections to remote computers through the network 4 which may comprise, for example, a local network or a wide area network (e.g., the Internet). The client computer 2 may connect to the network 4 through a network interface unit 16 connected to the bus 10. It should be appreciated that the network interface unit 16 may also be utilized to connect to other types of networks and remote computing systems. The client computer 2 may also include an input/output controller 22 for receiving and processing input from a number of input types, including a keyboard, mouse, pen, stylus, finger, and/or other means. Similarly, the input/output controller 22 may provide output to a display device 82, a printer, or other type of output device. Additionally, a touch screen can serve as an input and an output mechanism. It should be appreciated that the report server 70 and the back office server 80, shown in FIG. 1, may include many of the conventional components shown and discussed above with respect to the client computer 2.

Figure 3:
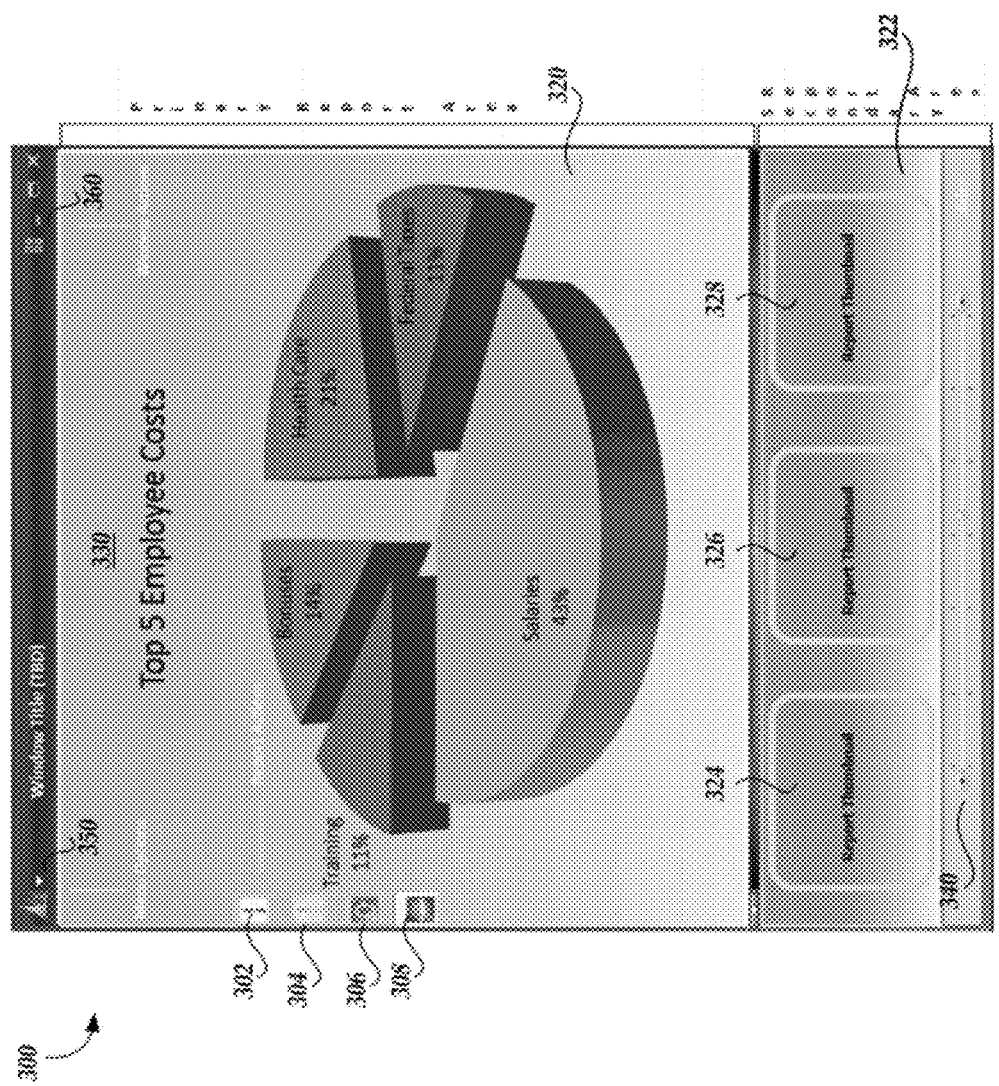
FIG. 3 is a computer screen display of a series of reports within a single user interface, in accordance with an embodiment.

FIG. 3 is a computer screen display of a series of reports within a single user interface 300, in accordance with an embodiment. The user interface 300 may be generated by the client application 30 (or alternatively, the client application 30 in use with the EP/CRM application 40) for display on the display device 82 connected to the client computer 2. The user interface 300 may display a report image 330 consisting of a chart (e.g., a pie chart of "Top 5 Employee Costs") in a primary report area 320. The user interface 30 may further include report action buttons 302-308 for initiating the communication of various business processes with respect to the report 330. A description of report action button functionality is described in a related U.S. utility patent application entitled "Integrating Report Actions for a Series of Reports within a Single User Interface" having Ser. No. 12/985,208, which was filed on Jan. 5, 2011. The user interface 300 may further include a secondary report area 322 in which report thumbnail images 324, 326 and 328 may be displayed. The report images 324, 326 and 328 may represent reports which related to the report image 330 shown in the primary report area 320. In accordance with an embodiment, the secondary report area 322 may be "docked" below the primary report area 320. However, it should be understood that the secondary report area 322 may also be docked to other sides of the user interface 300. The user interface 300 may also include a navigation slider 340 which may be utilized for navigating from the report images 324, 326 and 328 in the secondary report area 322 to other report images (not shown) which may also be contained within the secondary report area 322. The user interface 300 may also include a menu options control 350. In accordance with an embodiment, the menu options control 350 may provide various menu options for viewing a series of reports (i.e., a report series) as images in the user interface 300. In particular, the menu options control 350 may provide a menu option which may allow a user to change a currently selected report series for display in the primary report area 320 and the secondary report area 322 in the user interface 300. The user interface 300 may also include a window actions control 360. In accordance with an embodiment, the window actions control 360 may be utilized to select commands for manipulating the display of report images in a report series within the primary report area 320 and the secondary report area 322 in the user interface 300. In particular, the window actions control 360 may enable a user to move report images from the secondary report area 322 to the primary report area 320 in response to receiving a selected command.

Figure 4:
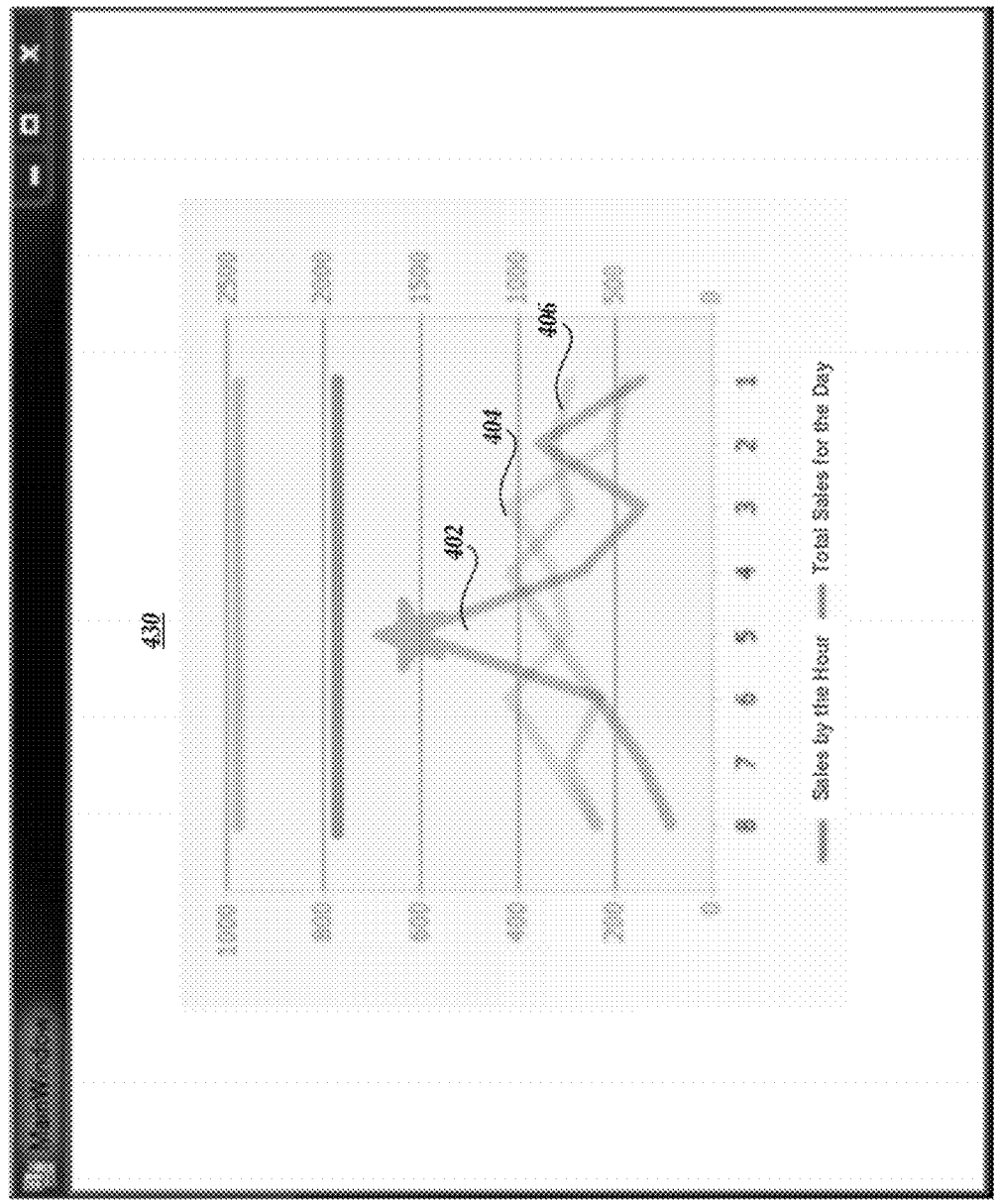
FIG. 4 is a computer screen display of a series of overlaid reports in a single user interface, in accordance with an embodiment.

FIG. 4 is a computer screen display of a series of overlaid reports in a single user interface 400, in accordance with an embodiment. The user interface 400 may be generated by the client application 30 (or alternatively, the client application 30 in use with the EP/CRM application 40) for display on the display device 82 connected to the client computer 2. The user interface 400 may display a report image 430 consisting of overlaid report images 402, 404 and 406. In particular, the client application 30 may be configured to combine reports taken from a secondary report area (not shown) to create the overlaid report image 430 in a primary report area of the user interface 400. It should be appreciated that overlaid reports may allow a user to see differences over time for a specified metric in a single report image.

Figure 5:
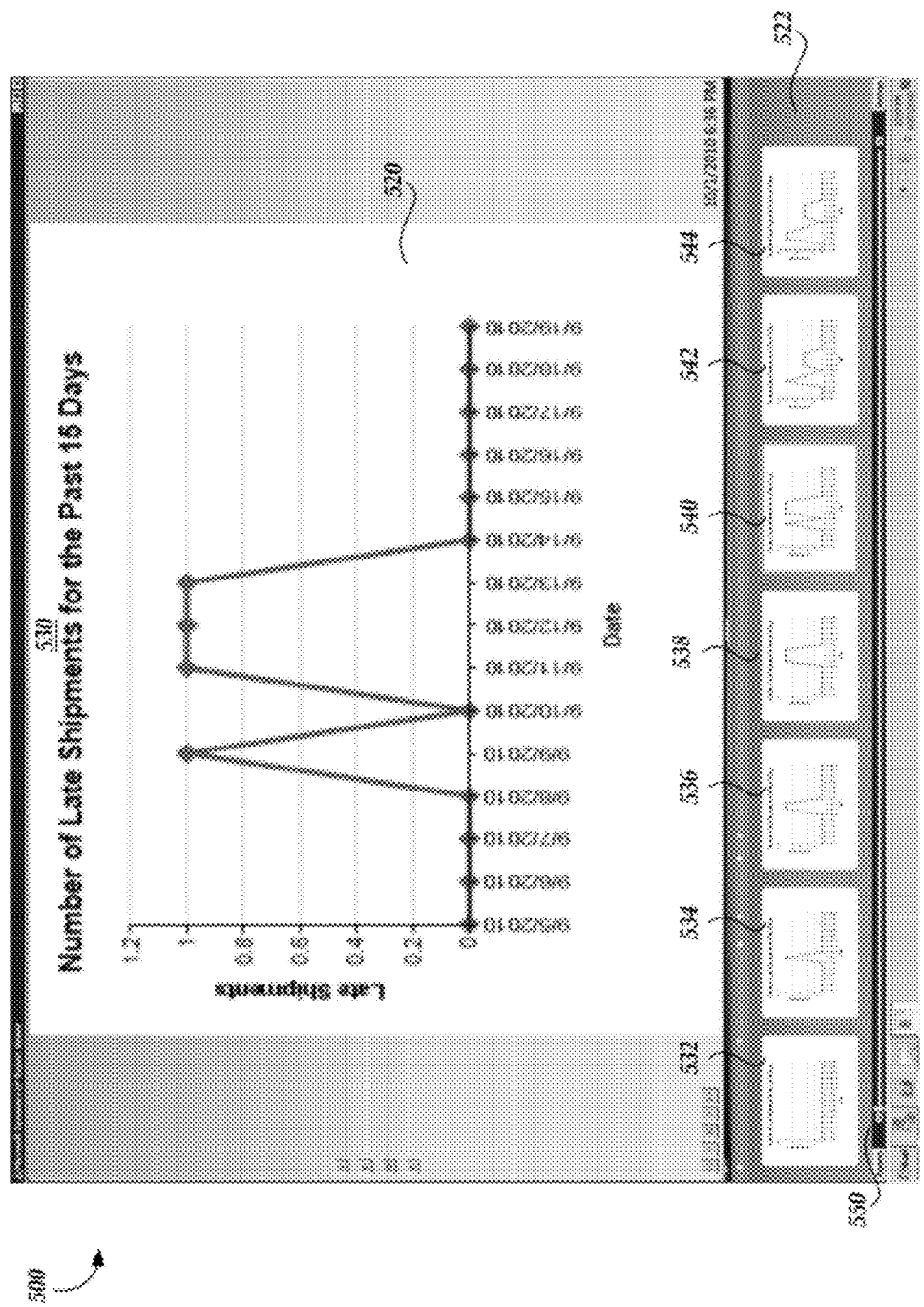
FIG. 5 is a computer screen display of trend data generated from a series of reports within a single user interface, in accordance with an embodiment.

FIG. 5 is a computer screen display of trend data generated from a series of reports within a single user interface 500, in accordance with an embodiment. The user interface 500 may be generated by the client application 30 (or alternatively, the client application 30 in use with the EP/CRM application 40) for display on the display device 82 connected to the client computer 2. The user interface 500 may display a report image 530 consisting of a graph (e.g., a line graph of "Number of Late Shipments for the Past 15 Days") in a primary report area 520. The user interface 500 may further include a secondary report area 522 in which report thumbnail images 532, 534, 536, 538, 540, 542 and 544 may be displayed. The report images 532-544 daily late shipment reports which are summarized by the line graph in the report image 530 displayed in the primary report area 520. Thus, the line graph in the report image 530 may be utilized to view a trend in late shipments over a specific period of time. The user interface 500 may also include a navigation slider 550 which may be utilized for navigating among the report images 532-544 in the secondary report area 522 as well as other off-screen report images (not shown) which may also be contained within the secondary report area 522.

Figure 6:
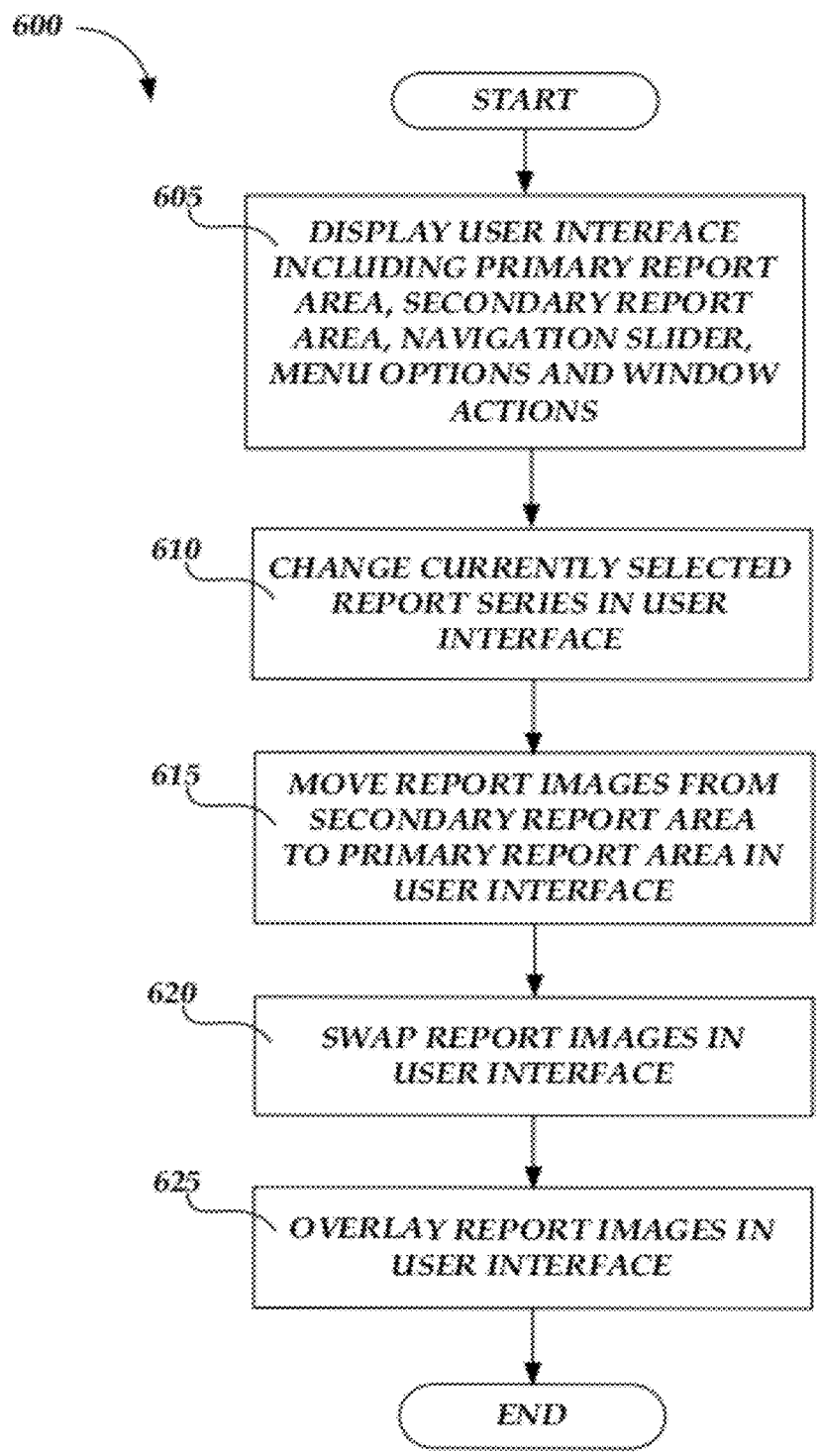
FIG. 6 is a flow diagram illustrating a routine for displaying a series of reports within a single user interface, in accordance with an embodiment.

FIG. 6 is a flow diagram illustrating a routine 600 for displaying a series of reports within a single user interface, in accordance with an embodiment. When reading the discussion of the routine presented herein, it should be appreciated that the logical operations of various embodiments of the present invention are implemented (1) as a sequence of computer implemented acts or program modules running on a computing system and/or (2) as interconnected machine logical circuits or circuit modules within the computing system. The implementation is a matter of choice dependent on the performance requirements of the computing system implementing the invention. Accordingly, the logical operations illustrated in FIG. 6 and making up the various embodiments described herein are referred to variously as operations, structural devices, acts or modules. It will be recognized by one skilled in the art that these operations, structural devices, acts and modules may be implemented in software, in firmware, in special purpose digital logical, and any combination thereof without deviating from the spirit and scope of the present invention as recited within the claims set forth herein.

The routine 600 begins at operation 605, where the client application 30 executing on the client computer 2 may display the user interface 300 including the primary report area 320, the report image 330, the secondary report area 322, the report images 324-328, the navigation slider 340, the menu options control 350, the window actions control 360 and the action buttons 302-308.

From operation 605, the routine 600 continues to operation 610, where the client application 30 may (in response to user input) change a currently selected report series in the user interface 300. In particular, a user may select an option from the menu options control 350 in the user interface 300 to change a currently selected report series (e.g., "Top 5 Employee Costs") to another report series (e.g., "Number of Late Shipments"), thereby generating the display of report images in the user interface 300 which are associated with the newly selected report series.

From operation 610, the routine 600 continues to operation 615, where the client application 30 may (in response to user input) move report images from the primary report area 320 to the secondary report area 322 in the user interface 300. In particular, a user may select an option from the window actions control 360 in the user interface 300 to move the report images from the secondary report area 322. In accordance with an embodiment, the window actions control 360 may allow a user to select a "Dashboard Mode" which, when selected, causes the client application 30 to automatically add all of the report images in the secondary report area 322 to the primary report area 320. In the aforementioned embodiment, the report images may be added down and then across the primary report area 320 in the order in which they appeared in the secondary report area 322. The client application 30 may further scale all of report images in the primary report area 320 so that the size of the report images are displayed in proportionately relative to the size of the primary report area 320. In this embodiment, client application 30 may further hide the secondary report area 322 (now empty) in the user interface 300 since there are no longer any displayed report images.

From operation 615, the routine 600 continues to operation 620, where the client application 30 may (in response to user input) swap a report image (i.e., the report image 330) displayed in the primary report area 320 with a selected report image in the secondary report area 322. In accordance with an embodiment, a user of the client application 30 may swap report images by clicking on a report image in the secondary report area 322 to select it. In response to the aforementioned user input, the client application 30 then swaps the report image 330 in the primary report area 320 with the selected report image in the secondary report area 322.

From operation 620, the routine 600 continues to operation 625, where the client application 30 may (in response to user input) overlay a series of report images in the user interface 400. For example, as discussed above with respect to FIG. 4, a user of the client application 30 may combine reports taken from a secondary report area to create the overlaid report image 430 in a primary report area of the user interface 400. It should be appreciated that overlaid reports may allow a user to see differences over time for a specified metric in a single report image. From operation 625 the routine 600 ends.

It should be understood that, in accordance with various embodiments, the client application 30 may be utilized to conduct other operations with respect to displayed report images in a user interface, such as the user interface 300. For example, the client application 30 may be configured to allow a user to delete non-relevant report images from the secondary report area 322 and retain report images where trends may be identified by a user. The user interface 300 generated by the client application 30 may further be utilized by a user to create a slide presentation playing a series of historical report images (in chronological order) displayed in the primary report area 320 and the secondary report area 322.

Although the invention has been described in connection with various illustrative embodiments, those of ordinary skill in the art will understand that many modifications can be made thereto within the scope of the claims that follow. Accordingly, it is not intended that the scope of the invention in any way be limited by the above description, but instead be determined entirely by reference to the claims that follow.

What is claimed is:

1. A method for displaying a series of report images within a user interface, the method implemented in a computing environment, the method comprising:

instructing a computer to display the user interface comprising:

a primary report area configured to display a first report image associated with a first report in a report series; and a secondary report area configured to display a plurality of other report images associated with other reports in the report series, the secondary report area being displayed concurrently with and adjacent to the primary report area;

receiving a first selection of a second report image of the plurality of other report images;

in response to the first selection of the second report image, instructing the computer to:

proportionally scale the second report image; and create a first overlaid report image in the primary report area by combining the scaled second report image with the first report image;

receiving a second selection of a third report image of the plurality of other report images; and in response to the second selection of the third report image, instructing the computer to:

proportionally scale the third report image; and swap the scaled third report image for the scaled second report image to create a second overlaid report image in the primary report area by combining the scaled third report image with the first report image.

2. The method of claim 1, further comprising:

instructing the computer to display a user control for selecting a plurality of menu options in the user interface, the plurality of menu options comprising commands for viewing the report series as images in the user interface.

3. The method of claim 2, further comprising:

instructing the computer to change a currently selected report series for display in the user interface in response to receiving a selected menu option from the plurality of menu options.

4. The method of claim 1, further comprising:

instructing the computer to display a user control for selecting commands associated with manipulating the display of a plurality of report images associated with a plurality of reports in the report series within the primary report area and the secondary report area in the user interface.

5. The method of claim 1, further comprising instructing the computer to:

analyze at least one of the first report and the second report to identify at least one action indicated by at least one of the first report and the second report;

create at least one custom action control for initiating the at least one action; and display the at least one custom action control and the overlaid report image in the primary report area of the user interface.

6. The method of claim 5, further comprising:

receiving a selection of the at least one custom action control; and instructing the computer to initiate the at least one action from the user interface.

7. The method of claim 5, wherein the at least one action comprises at least one of:

send a communication;

place an order;

create a purchase order;

make a phone call;

generate an offer; and initiate an employee compensation change.

8. A computer system for displaying a series of reports within a user interface, comprising:
 a memory for storing program code; and
 a processor, functionally coupled to the memory, the processor being responsive to computer-executable instructions contained in the program code and operative to:
  display the user interface, comprising:
   a primary report area configured to display a first report image associated with a report in a report series; and
   a secondary report area configured to display a plurality of other report images associated with other reports in the report series, the secondary report area being displayed concurrently with and adjacent to the primary report area;
  receive a first selection of a second report image of the plurality of other report images;
  in response to the first selection of the second report image,
   proportionally scale the second report image, and
   combine the scaled second report image with the first report image to create a first overlaid report image in the primary report area;
  receive a second selection of a third report image of the plurality of other report images;
  in response to the second selection of the third report image,
   proportionally scale the third report image, and
   swap the scaled third report image for the scaled second report image to create a second overlaid report image in the primary report area by combining the scaled third report image with the first report image.

9. The system of claim 8, wherein the processor is further operative to display a user control for selecting a plurality of menu options in the user interface, the plurality of menu options comprising commands for viewing the report series as report images in the user interface.

10. The system of claim 9, wherein the processor is further operative to change a currently selected report series for display in the user interface in response to receiving a selected menu option from the plurality of menu options.

11. The system of claim 8, wherein the processor is further operative to display a user control for selecting commands associated with manipulating the display of a plurality of report images associated with a plurality of reports in the report series within the primary report area and the secondary report area in the user interface.

12. The system of claim 8, further comprising receiving instructions to:
 analyze at least one of the first report and the second report to identify at least one action indicated by at least one of the first report and the second report;
 create at least one custom action control for initiating the at least one action; and
 display the at least one custom action control and the overlaid report image in the primary report area of the user interface.

13. The system of claim 12, further comprising:
 receive a selection of the at least one custom action control; and
 initiate the at least one action from the user interface.

14. The system of claim 12, wherein the at least one action comprises at least one of:
 send a communication;
 place an order; and
 make a phone call.

15. A computer-readable storage medium storing computer executable instructions which, when executed in a computing environment, cause a computer to perform a method for displaying a series of reports within a single user interface, the method comprising:
 receiving instructions to display a user interface comprising:
  a primary report area configured to display a first report image associated with a first report in a report series;
  a secondary report area configured to display a plurality of other report images associated with other reports in the report series, wherein the secondary report area is displayed concurrently with and adjacent to the primary report area;
  a first user control for selecting a plurality of menu options in the user interface, the plurality of menu options comprising commands for viewing the report series as images in the single user interface; and
  a second user control for selecting commands associated with manipulating the display of a plurality of report images associated with a plurality of reports in the report series within the primary report area and the secondary report area in the single user interface;
 receiving a first selection of a second report image of the plurality of other report images;
 in response to the first selection of the second report image, receiving instructions to:
  proportionally scale the second report image; and
  create a first overlaid report image in the primary report area by combining the scaled second report image with the first report image;
 receiving a second selection of a third report image of the plurality of other report images; and
 in response to the second selection of the third report image, instructing the computer to:
  proportionally scale the third report image; and
  swap the scaled third report image for the scaled second report image to create a second overlaid report image in the primary report area by combining the scaled third report image with the first report image.

16. The computer-readable storage medium of claim 15, further comprising receiving instructions to change a currently selected report series for display in the single user interface in response to receiving a selected menu option from the plurality of menu options.

17. The computer-readable storage medium of claim 15, wherein displaying the single user interface comprising the secondary report area comprises displaying the plurality of other report images in a chronological order.

18. The computer-readable storage medium of claim 15, further comprising receiving instructions to:
 analyze at least one of the first report and the second report to identify at least one action indicated by at least one of the first report and the second report;
 create at least one custom action control for initiating the at least one action; and
 display the at least one custom action control and the overlaid report image in the primary report area of the user interface.

19. The computer-readable storage medium of claim 18, further comprising:
 receiving a selection of the at least one custom action control; and
 receiving instructions to initiate the at least one action from the user interface.

20. The computer-readable storage medium of claim 18, wherein the at least one action comprises at least one of:
 send a communication;
 place an order;
 create a purchase order;
 make a phone call;
 generate an offer; and
 initiate an employee compensation change.

\* \* \* \* \*